United States Patent [19]

Weber et al.

[11] 4,263,460

[45] Apr. 21, 1981

[54] PROCESS FOR PREPARING METHYL-NONYL-ACETALDEHYDE

[75] Inventors: Jürgen Weber; Helmut Springer, both of Oberhausen, Fed. Rep. of Germany

[73] Assignee: Ruhrchemie Aktiengesellschaft, Oberhausen, Fed. Rep. of Germany

[21] Appl. No.: 106,299

[22] Filed: Dec. 21, 1979

[30] Foreign Application Priority Data

Dec. 22, 1978 [DE] Fed. Rep. of Germany ....... 2855506

[51] Int. Cl.³ ............................................. C07C 47/06
[52] U.S. Cl. ................................... 568/457; 568/449; 568/454
[58] Field of Search ........................ 568/449, 454, 457

[56] References Cited

U.S. PATENT DOCUMENTS

| | | | |
|---|---|---|---|
| 3,448,158 | 6/1969 | Slaugh et al. | 568/454 |
| 3,959,386 | 5/1976 | Pinke | 568/454 |
| 3,981,925 | 9/1976 | Schwager | 568/454 |

*Primary Examiner*—Paul J. Killos
*Attorney, Agent, or Firm*—Sprung, Felfe, Horn, Lynch & Kramer

[57] ABSTRACT

In a process for preparing methyl-nonyl-acetaldehyde from undecanal and formaldehyde or a source of formaldehyde, e.g., a substance which forms formaldehyde, in the presence of catalytic amounts of a secondary amine, the improvement wherein A. the undecanal is used in the form of the reaction mixture obtained by hydroformylation of 1-decene, and
B. di-n-butylamine is used as the catalyst,
C. the molar ratio of catalyst to undecanal is 0.025 to 0.050 to 1,
D. the reaction is carried out at 90° to 100° C., and
E. the 2-methylene-undecanal formed is then converted by partial hydrogenation into methyl-nonyl-acetaldehyde.

1 Claim, No Drawings

PROCESS FOR PREPARING METHYL-NONYL-ACETALDEHYDE

BACKGROUND OF THE INVENTION

1. Field of the Invention

This invention relates to the preparation of methyl-nonyl-acetaldehyde by reacting undecanal and formaldehyde or a compound which forms formaldehyde in the presence of a secondary amine.

2. Discussion of the Prior Art

Methyl-nonyl-acetaldehyde (2-methylundecanal) is a sought-after principal in perfumery because of its strong frangrance of oranges and incense.

A number of processes are known for preparing methyl-nonyl-acetaldehyde. Thus, according to one process, methyl-nonyl-ketone is reacted with ethyl chloroacetate to form the disubstituted glycidic ester, and the ester is then hydrolyzed with sodium hydroxide and, after acidification, converted into the aldehyde by steam distillation. (See Ullmans Enzyklopädie der technischen Chemie, 3rd edition, Vol. 14, page 737).

Another synthesis starts from n-undecanol, which is reacted with methanol in the presence of sodium methylate. 2-methyl-undecanol is formed, which is then dehydrogenated to form the aldehyde. (Chemical Abstracts Vol. 74 [1971], 12552 X.)

The preparation of α-methylenealdehydes is described in German 16 18 528. Aldehydes of the general formula $RCH_2CHO$ (where R denotes an alkyl group with 7-10 carbon atoms) are reacted with formaldehyde or substances forming formaldehyde, in the presence of a catalytic amount of ammonia or a primary or secondary amine or salts thereof. The corresponding α-methylaldehydes, of which α-methyl-nonyl-acetaldehyde is one example, are then obtained by hydrogenation.

The known methods for obtaining methyl-nonyl-acetaldehyde require the use of pure starting substances that are difficult to obtain. There is, therefore, the problem of providing a process for preparing the aforementioned aldehyde which permits the use of starting substances that are industrially available at low cost.

SUMMARY OF THE INVENTION

The invention provides a process for preparing methyl-nonyl-acetaldehyde from undecanal and formaldehyde or a substance forming formaldehyde, in the presence of catalytic amounts of a secondary amine, wherein undecanal is used in the form of the reaction mixture obtained in the hydroformylation of 1-decene and di-n-butylamine is used as catalyst, the molar ratio of catalyst to undecanal is 0.025 to 0.050 to 1, the reaction is carried out under normal pressure at 90°–100° C., and the 2-methyleneundecanal formed is then converted by partial hydrogenation into methyl-nonyl-acetaldehyde.

Compared to the known processes, the procedure according to the invention has the advantage that it starts from an easily obtainable raw material, namely, n-decene. The hydroformylation of this olefin, i.e., its conversion with carbon monoxide and hydrogen, is a known and widely used reaction. (J. Am. Chem. Soc. 78, 5401–5, [1956] J. Wender/Chem. Ber. 1969, 102 [7], 2238–40, Heil, Marko.) The reaction is normally carried out using metals of Group VIII of the Periodic System as catalyst, in particular cobalt or rhodium. The reaction conditions depend on the nature of the catalyst.

The cobalt-catalyzed conversion requires pressure of between 180 and 260 atmospheres and temperatures of 100°–150° C. The cobalt catalyst is used in an amount, calculated as the metal, of about 1 percent by weight, referred to the olefin employed. Rhodium, as catalyst, is used in lower concentrations, namely, in an amount of 1 to 100 mg Rh/kg of olefin used. In this case, the reaction is normally carried out with about 10 mg Rh/kg of olefin at temperatures of 90° to 150° C., preferably 120° to 130° C., and pressures of 150 to 300 atmospheres, preferably 270–290 atmospheres.

The reaction product obtained in the hydroformylation is not uniform. Decane as well as esters and alcohols are obtained in addition to the n- and iso-aldehyde. The following is a typical quantitative composition for the reaction product formed in the cobalt-catalyzed hydroformylation:

| | |
|---|---|
| Hydrocarbons | 8.0 percent |
| Iso-undecanal | 22.0 percent |
| n-undecanal | 53.0 percent |
| Esters and alcohols | 17.0 percent |

When using rhodium as catalyst, a mixture of approximately the following composition is obtained:

| | |
|---|---|
| Hydrocarbons | 2.0 percent |
| Iso-undecanal | 65.0 percent |
| n-undecanal | 32.0 percent |
| Esters and alcohols | 1.0 percent |

According to the invention, the reaction mixture freed from the catalyst is directly converted, without prior separation into its constituents, with formaldehyde or a substance forming formaldehyde, e.g., paraformaldehyde, in the presence of di-n-butylamine at 90°–100° C.

The reaction can be carried out batchwise or continuously in a vessel provided with a stirrer, the amount of formaldehyde and di-n-butylamine required for the synthesis being calculated on the basis of the amount of n-undecanal contained in the hydroformylation product. The reaction is complete after 60–120 minutes. A particular advantage of the new process is that by choosing a specific catalyst as well as optimum temperature conditions, a high conversion, up to 98 percent of the aldehyde employed is converted into the desired reaction product, can be achieved.

After phase separation, the reaction product is partially hydrogenated with the aid of catalysts. Suitable catalysts for this hydrogen addition are precious metal catalysts, in particular palladium or platinum catalysts containing $Al_2O_3$ or activated charcoal as carrier and 0.2 to 5 percent by weight of metal, referred to the total catalyst. Methyl-nonyl-acetaldehyde can then be obtained from this approximately 50 percent crude product by rectification (distillation). The partial hydrogenation is effected using hydrogen at a pressure of 1 to 200 atm. The partial hydrogenation is carried out at a temperature of 40° to 140° C. for 10 to 60 minutes.

The process according to the invention is described in more detail by means of the following example:

EXAMPLE 1000 g of a crude product obtained from 1-decene by cobalt-catalyzed hydroformylation and containing 55.2 percent of n-undecanal is stirred with 357 g of 30 percent formalin and 21 g or di-n-butylamine in a flask for 90 minutes under reflux. The reaction mixture is then cooled and the phases are separated. Gas chromatography analysis of the organic phase shows a 2-methylene-undecanal content of 55.4 percent, in addition to 1.2 percent of unreacted n-undecanal. The yield referred to 1-decene is 54 percent.

In the second reaction stage, the reaction mixture is partially hydrogenated with the aid of 1 percent by weight of catalyst (5 percent Pd on activated charcoal) referred to the aldehyde used. A crude product having the following composition is obtained:

| First runnings | 1.1 percent |
| --- | --- |
| Iso-undecanal | 29.2 percent |
| n-undecanal | 0.5 percent |
| 2-methylene-undecanal | <0.1 percent |
| Methyl-nonyl-acetaldehyde | 53.6 percent |
| Last runnings | 15.5 percent |

Methyl-nonyl-acetaldehyde can be separated in a purity of >95 percent from this crude product by fractional distillation.

What is claimed is:

1. In a process for preparing methyl-nonyl-acetaldehyde from undecanal and formaldehyde or a source of formaldehyde, e.g., a substance which forms formaldehyde, in the presence of catalytic amounts of a secondary amine, the improvement wherein
    A. the undecanal is used in the form of the reaction mixture obtained by hydroformylation of 1-decene, and
    B. di-n-butylamine is used as the catalyst,
    C. the molar ratio of catalyst to undecanal is 0.025 to 0.050 to 1,
    D. the reaction is carried out at 90° to 100° C., and
    E. the 2-methylene-undecanal formed is then converted by partial hydrogenation into methyl-nonyl-acetaldehyde.

* * * * *